(12) United States Patent
Pedersen et al.

(10) Patent No.: US 7,955,281 B2
(45) Date of Patent: Jun. 7, 2011

(54) EXTERNAL ULTRASOUND LIPOPLASTY

(75) Inventors: Laust G. Pedersen, Santa Barbara, CA (US); Bobby Purkait, Montecito, CA (US)

(73) Assignee: Nivasonix, LLC, Santa Barbara, CA (US)

( * ) Notice: Subject to any disclaimer, the term of this patent is extended or adjusted under 35 U.S.C. 154(b) by 671 days.

(21) Appl. No.: 11/518,367

(22) Filed: Sep. 7, 2006

(65) Prior Publication Data
US 2008/0097253 A1    Apr. 24, 2008

(51) Int. Cl.
*A61H 1/00*    (2006.01)
(52) U.S. Cl. ............................................. 601/2; 600/439
(58) Field of Classification Search ........................ None
See application file for complete search history.

(56) References Cited

U.S. PATENT DOCUMENTS

| | | |
|---|---|---|
| 2,283,285 A | 5/1942 | Pohlman |
| 2,559,227 A | 7/1951 | Rieber |
| 4,164,213 A | 8/1979 | Hoelzler |
| 4,525,359 A | 6/1985 | Greenway, III et al. |
| 4,528,979 A | 7/1985 | Marchenko et al. |
| 4,588,724 A | 5/1986 | Greenway, III et al. |
| 4,605,009 A | 8/1986 | Pourcelot et al. |
| 4,813,402 A | 3/1989 | Reichenberger et al. |
| 4,886,491 A | 12/1989 | Parisi et al. |
| 4,888,746 A | 12/1989 | Wurster et al. |
| 4,938,216 A | 7/1990 | Lele |
| 4,962,752 A | 10/1990 | Reichenberger et al. |
| 4,986,275 A | 1/1991 | Ishida et al. |
| 5,005,579 A | 4/1991 | Wurster et al. |
| 5,015,929 A | 5/1991 | Cathignol et al. |
| 5,079,952 A | 1/1992 | Nakaso et al. |
| 5,080,102 A | 1/1992 | Dory |
| 5,111,822 A | 5/1992 | Dory |
| 5,143,063 A | 9/1992 | Fellner |
| 5,143,073 A | 9/1992 | Dory |
| 5,158,070 A | 10/1992 | Dory |
| 5,209,221 A | 5/1993 | Riedlinger |
| 5,219,401 A | 6/1993 | Cathignol et al. |
| 5,291,890 A | 3/1994 | Cline et al. |

(Continued)

FOREIGN PATENT DOCUMENTS

DE    3150513    6/1983

(Continued)

OTHER PUBLICATIONS

Arner, P. "Adrenergic Receptor Function in Fat Cells," Am. J. Clin. Nutr. 1992: 55; pp. 228-236.

(Continued)

*Primary Examiner* — Unsu Jung
*Assistant Examiner* — Nigel Fontenot
(74) *Attorney, Agent, or Firm* — Blakely Sokoloff Taylor & Zafman LLP

(57) ABSTRACT

This invention relates to a non-invasive, safer alternative to current lipoplasty procedures. The preferred embodiment of the invention is a multi-channel system that focuses the low mega Hertz ultrasound at user selectable depths, where fat cells are to be emulsified. The system has independent user control of the main emulsifying property, cavitation, and thermal heating, which can independently be used for skin tightening. One part of the system is a handheld transducer, in shape similar to a typical small diagnostic ultrasound transducer. The other part of the system includes a transmitter with internal tracking of procedure time and with a disabling feature.

21 Claims, 11 Drawing Sheets

U.S. PATENT DOCUMENTS

| | | | |
|---|---|---|---|
| 5,301,660 | A | 4/1994 | Rattner |
| 5,419,761 | A | 5/1995 | Narayanan et al. |
| 5,431,621 | A | 7/1995 | Dory |
| 5,507,790 | A | 4/1996 | Weiss |
| 5,514,086 | A | 5/1996 | Parisi et al. |
| 5,526,815 | A | 6/1996 | Granz et al. |
| 5,527,273 | A | 6/1996 | Manna et al. |
| 5,601,526 | A | 2/1997 | Chapelon et al. |
| 5,618,275 | A | 4/1997 | Bock |
| 5,640,371 | A | 6/1997 | Schmidt et al. |
| 5,704,105 | A * | 1/1998 | Venkataramani et al. ... 29/25.35 |
| 5,725,482 | A | 3/1998 | Bishop |
| 5,743,863 | A | 4/1998 | Chapelon |
| 5,769,879 | A | 6/1998 | Richards et al. |
| 5,823,990 | A | 10/1998 | Henley |
| 5,827,204 | A | 10/1998 | Grandia et al. |
| 5,884,631 | A | 3/1999 | Silberg |
| 5,938,608 | A | 8/1999 | Bieger et al. |
| 6,013,048 | A | 1/2000 | Podany et al. |
| 6,032,675 | A | 3/2000 | Rubinsky |
| 6,033,375 | A | 3/2000 | Brumbach |
| 6,036,644 | A | 3/2000 | Schutt |
| 6,039,048 | A | 3/2000 | Silberg |
| 6,045,777 | A | 4/2000 | Church et al. |
| 6,071,239 | A * | 6/2000 | Cribbs et al. .................. 600/439 |
| 6,086,535 | A | 7/2000 | Ishibashhi et al. |
| 6,106,511 | A | 8/2000 | Jensen |
| 6,113,558 | A | 9/2000 | Rosenschein et al. |
| 6,113,559 | A | 9/2000 | Klopotek |
| 6,135,971 | A | 10/2000 | Hutchinson et al. |
| 6,156,549 | A | 12/2000 | Drewes et al. |
| 6,206,873 | B1 | 3/2001 | Paolini et al. |
| 6,350,245 | B1 | 2/2002 | Cimino |
| 6,384,516 | B1 | 5/2002 | Fraser |
| 6,607,498 | B2 | 8/2003 | Eshel |
| 6,626,854 | B2 | 9/2003 | Friedman et al. |
| 6,645,162 | B2 | 11/2003 | Friedman et al. |
| 6,946,098 | B2 | 9/2005 | Miekka et al. |
| 2002/0082528 | A1 * | 6/2002 | Friedman et al. .................. 601/2 |
| 2002/0128592 | A1 * | 9/2002 | Eshel ................ 604/22 |
| 2003/0236487 | A1 * | 12/2003 | Knowlton ........................ 604/20 |
| 2004/0001809 | A1 * | 1/2004 | Brisken et al. ............. 424/93.21 |
| 2004/0039312 | A1 * | 2/2004 | Hillstead et al. .................. 601/2 |
| 2004/0043376 | A1 * | 3/2004 | Gupta ............................... 435/4 |
| 2005/0240126 | A1 * | 10/2005 | Foley et al. ........................ 601/2 |
| 2006/0074313 | A1 * | 4/2006 | Slayton et al. ................. 600/439 |
| 2006/0094988 | A1 * | 5/2006 | Tosaya et al. ...................... 601/2 |
| 2006/0122509 | A1 * | 6/2006 | Desilets ........................ 600/439 |

FOREIGN PATENT DOCUMENTS

| | | |
|---|---|---|
| DE | 4006762 | 9/1991 |
| EP | 0256202 | 2/1988 |
| EP | 0330816 | 9/1989 |
| EP | 0363239 | 4/1990 |
| FR | 2639238 | 5/1990 |
| GB | 820814 | 9/1959 |
| GB | 2167305 | 5/1986 |
| GB | 2303552 | 2/1997 |

OTHER PUBLICATIONS

Babbs, C., et al. "Equipment for Local Hyperthermia Therapy of Cancer," Medical Instrumentation 1982: vol. 16, No. 5, pp. 245-248.

Bates, B. "External Ultrasound's Liposuction Role Debated," http://molecularmedicine.medscape.com/IMNG/SkinAllergyNews/19.../san3003.06.02.htm, Mar. 17, 2000; pp. 1-2.

Bommannan, D., et al. "Sonophoresis. I. The Use of High-Frequency Ultrasound to Enhance Transdermal Drug Delivery," Pharmaceutical Research, vol. 9, No. 4, 1992; pp. 559-564.

Cheung, A., et al. "Deep Local Hyperthermia for Cancer Therapy: External Electromagnetic and Ultrasound Techniques," Cancer Research (Suppl.) 44, 1984; pp. 4736-4744.

Dunn, et al. "Ultrasonic Threshold Dosages for the Mammalian Central Nervous System," IEEE Transactions on Bio-Medical Engineering, 18:4, 253-256, Jul. 1971.

Eisenhauer, K. "6/24-Ultrasound Liposuction," http://www.channel6000.com/health/health-990624-191707.html, Mar. 17, 2000, pp. 1-2.

Greenway, F., et al. "Regional Fat Loss from the Thigh in Obese Women after Adrenergic Modulation," Clinical Therapeutics, vol. 9, No. 6, 1987; pp. 663-669.

Hofmann, D., et al. "The Effect of Ultrasound on In-Vitro Liberation and In Vivo Penetration of Benzyl Nicotinate," Journal of Controlled Release, 27 (1993), pp. 185-192.

Hunt, J. "Principles of Ultrasound used for Generating Localized Hyperthermia," in An Introduction to the Practical Aspects of Clinical Hyperthermia, Taylor & Francis, Lond, 1990; pp. 371-418.

Lalonde, R., et al. "Field Conjugate Acoustic Lenses for Ultrasound Hyperthermia," IEEE Transactions on Ultrasonics, Ferroelectrics, and Frequency Control, vol. 40, No. 5, Sep. 1993; pp. 592-602.

LeVeen, H., et al. "Tumor Eradication by Radiofrequency Therapy," JAMA, May 17, 1976—vol. 235, No. 20; pp. 2198-2200.

Nigro, D.M. "Ultrasound Assisted Lipoplasty (Liposuction)," http://www.drnigro.com/dennis.htm, Mar. 17, 2000, p. 1.

Ocheltree, K., et al. "Sound Field Calculation for Rectangular Sources," IEEE Transactions on Ultrasonics, Ferroelectrics, and Frequency Control, vol. 36, No. 2, Mar. 1989; pp. 242-248.

Rohrich, R., et al. "Comparative Lipoplasty Analysis of In Vivo-Treated Adipose Tissue," Plastic and Reconstruction Journal, 105:2152-2158, 2000.

Wahrenberg, H., et al. "Mechanisms Underlying Regional Differences in Lipolysis in Human Adipose Tissue," J. Clin. Invest. vol. 84, Aug. 1989; pp. 458-467.

Wang, H., et al. "Computationally Efficient Algorithms for Control of Ultrasound Phased-Array Hyperthermia Applicators Based on a Pseudoinverse Method," IEEE Transactions on Ultrasonics, Ferroelectrics, and Frequency Control, vol. 17, No. 2, May 1990; pp. 274-276.

Yang, W., et al. "Shortwave and Microwave Diathermy for Deep-Tissue Heating," Med. Biol. Eng. & Comput., 1979, vol. 17, pp. 518-523.

"Glossary," http://lipoinfo.com/glossary.htm, Mar. 17, 2000, pp. 1-14.

"Body Sculpting/Liposuction," http://www.cosmeticdoctor.com/sculpting.htm, Mar. 17, 2000, pp. 1-3.

"External Ultrasonic Liposuction," http://www.lipoinfo.com/chap14.htm, Mar. 17, 2000, p. 1.

"For Ultrasonic Liposuction," http://www.ultrasonic-liposuction.com/index.html, Mar. 17, 2000, p. 1.

"Internal, External Ultrasound Aids Liposuction," http://surgery.medscape.com/IMNG/SkinAllergyNews/1998/v.29.n03/san2903.46.01.html, Mar. 17, 2000, pp. 1-3.

"Liposuction," http://www.ultrasonic-liposuction,com/informationA.html, Mar. 17, 2000, pp. 1-2.

"Liposuction," http://www.swmed.edu/home_pages/library/consumer/liposuc.htm, Mar. 17, 2000, p. 1.

"Liquefying the Fat: Ultrasound Expands Scope of Liposuction," http://www.swmed.edu/home_pages/new/liquilip.htm, Mar. 17, 2000, 1-2.

"The Lipo Symposium," http://liposymposium.com/details/History, Mar. 17, 2000, p. 1.

"Trends in Cosmetic Surgery: Lipoplasty (Liposuction)," http://www.wrc-gbmc.org/4rd.html, Mar. 17, 2001, p. 1.

"Ultrasound Liposuction (or Ultrasound Assisted Lipoplasty—UAL)," http://www.ultrasonic-liposuction.com/InformationD.html, Mar. 17, 2000, pp. 1-2.

"Ultrasound Assisted Lipoplasty," http://www.plasticsurgery.org/surgery/ual.htm, Mar. 17, 2000, pp. 1-4.

"Ultrasound-Assisted Liposuction," http://www.drhobar.com/ual.htm, Mar. 17, 2000, pp. 1-4.

"Ultrasonic-Assisted Liposuction," http://www.liposymposium.com/details/procedure/techniques/UAL, Mar. 17, 2000, pp. 1-2.

"Ultrasound-Assisted Liposuction," http://www.providence-hospital.org/technology/lipo.htm, Mar. 17, 2000, p. 1.

"Ultrasonic Liposuction; Body Contouring," http://www.drloomis.com/serv01.htm, Mar. 17, 2000, pp. 1-2.

NIVASONIX, LLC, "International Search Report dated Mar. 13, 2008", PCT/US07/077932.

Kossoff G, "Analysis of focusing action of spherically curved transducers" Ultrasound in Med & Biol 5;359-365:1979.

Weyns A "Radiation field calculations of pulsed ultrasonic transducers. Part 1" Ultrasonics pp. 183-188, Jul. 1980.

Weyns A "Radiation field calculations of pulsed ultrasonic transducers. Part 2" Ultrasonics pp. 219-223, Sep. 1980.

O'Neil HT et al, "Theory of focusing radiators" J Acous Soc Am 21:516-526:1949.

Tarnoczy T "Sound focusing lenses and waveguides" Ultrasonics pp. 115-127, Jul.-Sep. 1965.

Zagzebski JA et al. "Focused transducer beams in tissue-mimicking material" J Clin Ultrasound 10;159-166:1982.

Higgins FP et al. "Optical interferometric visualization and computerized reconstruction of ultrasonic fields"J Acous Soc Am 68;1169-1176:1980.

Jones DR et al. "Tissue attenuation effects on transducer performance" Medical Ultrasound 5;107-112:1981.

Zemanek J "Beam behavior within the nearfield of a vibrating piston" J Acous Soc Am 49;181-191:1970.

El-Sherbiny SM "The effect of range on the ultrasonic echo acting on circular and rectangular transceivers" Acustica 43;73-76:1979.

Hayman AJ et al. "Transmission and reception of short ultrasonic pulses by circular and square transducers" J Acous Soc Am 66;945-951:1979.

Hynynen K et al. "Design of ultrasonic transducers for local hyperthermia" Ultrasound in Med & Biol 7;397-402:1981.

NEMA Standards Publication UD Mar. 2004, "Standard for Real-Time Display of Thermal and Mechanical Acoustic Output Indices on Diagnostic Ultrasound Equipment," National Electrical Manufacturers Association, Rev. 2, 2004.

Food and Drug Administration, "Information for Manufacturers Seeking Marketing Clearance of Diagnostic Ultrasound Systems and Transducers," U.S. Dept. of Health and Human Services, 1997.

IEC 62359, "Ultrasonics—Field Characerization—Test Methods for the Determination of Thermal and Mechanical Indices Related to Medical Diagnostic Ultrasonic Fields," First edition, 2006, pp. 1-87.

Geisler, et al., "Acoustic Bubble Traps," Acoustical Society of America, ASA/EAA/DAGA 1999 Meeting, http://www.acoustics.org/press/137th/geisler.html.

Gompf, et al., "Studying Bubble Collapse on a Subnanometer Time Scale," Acoustical Society of America, ASA/EAA/DAGA 1999 Meeting, http://www.acoustics.org/press/137th/gompf.html.

"Sonochemistry Images," European Society of Sonochemistry, 2002; http://www..fb-chemie.unirostock.de/ess/sonochem image.html.

* cited by examiner

EXTERNAL ULTRASOUND LIPOPLASTY

FIELD OF THE INVENTION

The present invention generally relates to the field of ultrasound lipoplasty. More particularly, the present invention relates to non-invasive lipoplasty, imaging and detection capability of fat layer and dissolution of emulsified fat by infusion of fat dissolution solvent.

BACKGROUND OF THE INVENTION

According to American Society for Aesthetic Plastic Surgery (ASAPS) statistics, liposuction is one of the most popular plastic surgery procedures performed in the world. Approximately 456,000 procedures were carried out in the year 2005 in the U.S. alone and the numbers are growing.

Although traditional suction-assisted lipoplasty (SAL) is the most widely used technique, several new technologies have emerged for the lipoplasty procedure. These growing numbers of lipoplasty techniques have come to be known by acronyms such as SAL, PAL, UAL, E-UAL, VAL and so on. A brief glossary and overview of these liposuction techniques are discussed below.

Suction-Assisted Lipoplasty (SAL):

Suction-assisted lipoplasty is a traditional method during which fat is removed by inserting a hollow tube (cannula) with radial holes near the blunt tip through one or more small incisions near the area to be suctioned. The cannula is connected by tubing to a vacuum pressure unit, sucking the adjacent tissue into the holes and tearing it off by the reciprocating motion performed by the surgeon. The tumescent technique is the prior infusion of saline solution with minute amounts of anesthetic and vasoconstriction drugs.

Power-assisted lipoplasty (PAL) is a variant of SAL using a powered reciprocating cannula which reduces surgeon efforts. Both procedures are tedious, have considerable complications and are non-discriminating as to what is being removed.

Ultrasound-Assisted Lipoplasty (UAL)

Ultrasound-assisted lipoplasty adds the emulsifying property of high intensity ultrasound (mainly cavitation and heating) by setting up a standing wave in the specialized cannulae typically in the 25-30 kHz range. UAL equipment normally also includes equipment for infiltration of tumescent fluid both prior to the procedure and during the emulsification and aspiration as irrigation. This enhances the emulsifying cavitation effect and reduces the inherent heating. The technology is similar to what is used in industrial ultrasound drilling and phacoemulsification.

Vaser-Assisted lipoplasty (VAL) is a variant of UAL using pulsed wave (PW) rather than continuous wave (CW) ultrasound, which has the potential for separating the cavitation and heating mechanisms.

SAL, UAL and their variations remove fat non-uniformly as tunnels in a fan-like geometry from the incision(s) often resulting in a non-uniform skin surface in spite of the fact that the patient is required to wear compression garment(s) for some weeks. The patient recovery time is long and the procedure beyond the typical risk of the often-used general anesthesia can lead to serious complications.

External UAL

External UAL (E-UAL), which uses external ultrasound that may emulsify fat cells within the body, is still in the earliest stages of scientific evaluation. E-UAL typically consists of "softening" adipose tissue by externally applying high intensity ultrasound and using standard lipoplasty cannulae to remove the "softened" fat. The current technology has its historical roots to therapeutic ultrasound, hence has a frequency in the 1 to 3.5 MHz range and similar transducer shapes. The prior art literature does not disclose intensity levels or focusing.

Currently, there are two types of E-UAL systems. The major differences between the two systems are the use of one transducer versus two transducers, and variations in the technique of fat removal. One system uses suction to remove the liquefied fat. The other method follows the external ultrasound treatment with massage and the application of compression foam and garments. These procedures do appear to have advantages over invasive liposuction with very few complications reported to date, however it has not been accepted as an efficacious process.

High Intensity Focused Ultrasound (HIFU)

High intensity focused ultrasound is designed as a tissue ablation device mainly to treat cancer with ultrasound induced hyperthermia, but would also have the ability to assist in E-UAL. The technology typically is combined with ultrasound diagnostic imaging.

It has been shown that under the right conditions, high intensity ultrasound has fat discriminating properties, which mean that blood vessels, nerve endings and connective tissue are left intact while fat cells are destroyed.

Recognizing the demand for liposuction, as well as the potential of having serious complications from each of the above technique, there is a significant opportunity for a safe and effective, less expensive and a user-friendly device that would provide benefits both to the surgeons and patients.

SUMMARY OF THE INVENTION

The present invention comprises a non-invasive, safer alternative to current invasive liposuction, one of the most commonly performed cosmetic procedures. In contrast to invasive surgical procedures in which emulsified fat is physically extracted, this novel and proprietary designed ultrasound device applies energy in a controlled manner transdermally and liquefies fat cells selectively within a very short period of time that destroy the fat cell walls. Emulsified fat is then metabolized and excreted from the body through natural processes, resulting in a safe outpatient procedure without resorting to general anesthesia.

Some aspects of the invention provide a single-channel external ultrasound lipoplasty (EUL) system comprising a transmitter and a single element transducer in the 0.5 MHz to 20 MHz frequency range, wherein the transducer consists of a substantially cylindrically shaped active transducer element with a fixed focus in the manufacturer selected depth range between about 1 mm and 30 mm, the transducer aperture and frequency being configured to not irreversibly affect tissue of a patient beyond the user or manufacturer selected depth range when an acoustic pressure and intensity of the EUL system is high enough to substantially emulsify fat within the selected depth range of the tissue.

Some aspects of the invention provide an external ultrasound lipoplasty (EUL) system comprising a transmitter and a multi-channel transducer operated in a 0.5 MHz to 20 MHz frequency range, wherein the transducer consists of a transducer aperture and an electronic focus that is electronically swept within a user or manufacturer selected depth range between about 1 mm and 30 mm, the transducer aperture and frequency being configured to not irreversibly affect tissue of a patient beyond the user or manufacturer selected depth range when an acoustic pressure and intensity of the EUL system is high enough to substantially emulsify fat within the selected depth range of the tissue. In one embodiment, the transducer is a multi-channel transducer with a 0.5D or 1.5D array.

Some aspects of the invention provide a method for emulsifying subdermal fat comprising topically applying ultrasound through a hand-held high intensity focused ultrasound transducer acoustically coupled to the skin overlaying the subdermal fat via a liquid or gel, the focused ultrasound transducer comprising a transmitter and a multi-channel transducer operated in a 0.5 MHz to 20 MHz frequency range, wherein the transducer consists of a transducer aperture and an electronic focus that is electronically swept within a user or manufacturer selected depth range between about 1 mm and 30 mm, wherein the transducer aperture and frequency being configured to not irreversibly affect tissue of a patient beyond the user or manufacturer selected depth range when an acoustic pressure and intensity of the focused ultrasound transducer is high enough to substantially emulsify the subdermal fat within the selected depth range of the tissue.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as conceived or suggested herein without necessarily achieving other advantages as may be conceived or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Figure 1:
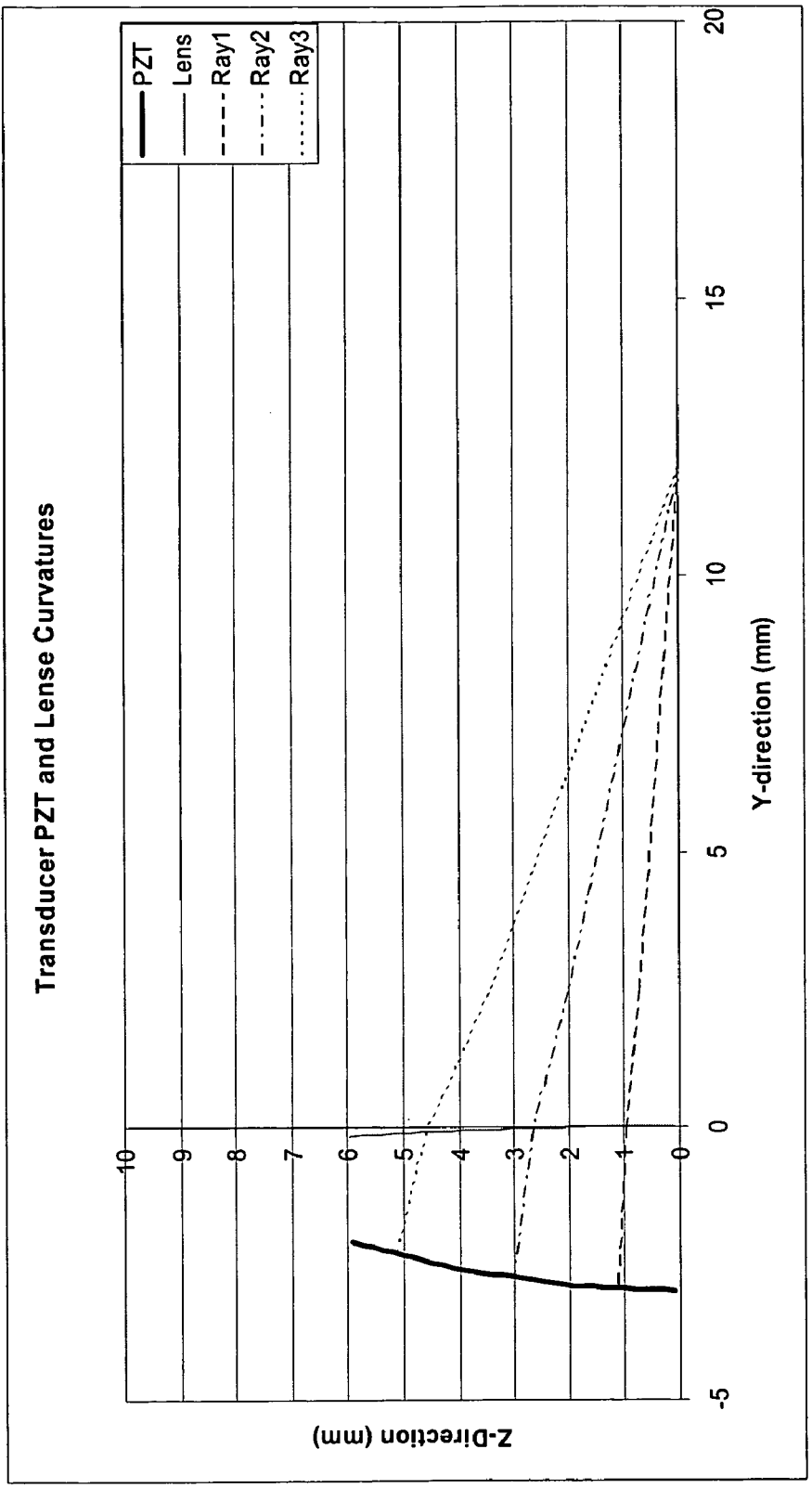
FIG. 1 shows the ray tracing of the transmitted ultrasound starting from the center of the individual element pair to the focal point with the x-axis being the depth and y-axis being the transverse direction. The input parameters are listed in Table 1.

The preferred embodiments of the invention described herein relate particularly to an external ultrasound lipoplasty system comprising a transmitter and a multi-channel transducer with the transducer aperture and frequency being configured to not irreversibly affect tissue of a patient beyond the user or manufacturer selected depth range when an acoustic pressure and intensity of the system is high enough to substantially emulsify fat within the selected depth range of the tissue. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The preferred embodiment of the invention is a multi-channel system that focuses the low mega Hertz ultrasound at user selectable depths, where fat cells are to be emulsified. The system has independent user control of the main emulsifying property, cavitation, and thermal heating, which can independently be used for skin tightening. One part of the system is a handheld transducer, in shape similar to a typical small diagnostic ultrasound transducer. The other part of the system includes a transmitter with internal tracking of procedure time and with a disabling feature.

A further expansion of the External Ultrasound Lipoplasty (EUL) system and methodology includes a cavitation detection feature based on running the transducer in pulse-echo mode, an adjacent ultrasound system to track the fat emulsification and with time the fat layer reduction, the infusion of a micro-solution that aid in fat call emulsification through chemical means and/or enhancing cavitation, a rolling device to better distribute the emulsified fat cells and a reagent strip for home test of urine samples to verify metabolized fat.

The External Ultrasound Lipoplasty (EUL) system described herein is intended to emulsify fat in a patient from 10 cc to a maximum of 500 cc fat tissues per treatment, thus providing great flexibility to patients and surgeons. Normally, 1000 to 5000 cc of fat is removed with the current single invasive liposuction operation, which may provide some benefits to some patients in saving time. However, such a large quantity of fat being removed in one session tends to cause trauma, blood loss and long recovery time. While removing fat in a smaller volume not only would minimize these severe complications, but also would provide a more subtle change in appearance as opposed to a sudden change in body appearance.

The technology would enable much smaller, controlled amounts of fat to be removed in an office-based procedure. The convenience and comfort of this procedure provided by the device of the present invention could make this a 'lunch hour' body sculpting treatment.

Due to the simplicity of the procedure and equipment and the drastically reduced staffing requirement, the cost of these procedures can similarly be priced to make it attractive to the customer. The design of the device and technique for liposuction would provide the capability of effectively tackling small areas of fat. The procedure would simply emulsify fat cells; the emulsified fat is metabolized and excreted through normal body function. There is no need for sucking out the liquefied fat using tube through insertion on the skin.

The clearance of metabolized fat byproducts would generally occur within one to two weeks which is dependent upon total volume of fat emulsified and also on each patient's physiological functioning mechanism.

The advantages of the present invention when compared to conventional methods include both patient and surgeon:

| A. Patient | B. Surgeon |
|---|---|
| "Lunch time" procedure | "Lunch time" procedure |
| Less time lost from work or other important engagements | Reduced procedure time |
| Fast/no recovery time | Less procedure Fatigue |
| Non-invasive procedure | Minimal staff required |
| Gradual change in appearance | No anesthesia needed |
| Better skin retraction | Fewer complication risks |
| Uniform fat removal | Potential for better patient satisfaction |
| No anesthesia | Anesthetic and sterilization equipment not needed |
| Little or no trauma | More competitive |
| Less ecchymoses | Allows for more controlled body sculpting |
| Less bleeding | On-going treatment ability for maintenance |
| Less edema | No cost for operating room and other related expenses |
| Less hematoma | No big investment for equipment and devices |
| No transfusion | No capital investment (lease) |
| Less potential for skin damage (burning or bruising) | "Worry free" equipment (free service) |
| Less post-op pain | "Worry free" equipment upgrade (free) |
| More flexibility in control of time and procedure | Repeat procedures give opportunity for efficacy assessment |
| Additive effect of repeat treatment possible | |
| Low Cost | Office based |

To provide the above-identified benefits and desired advantages over other products, seven major aspects were considered:

1. An innovative handheld and simple transducer with electronic focus.

2. An integrated skin temperature sensing method.

3. A system where the user has independent control of the cavitation level, Mechanical Index (MI), the heat generation Thermal Index (TI) and the depth range for emulsification (electronic focus). The MI and TI are herein defined per AIUM/NEMA's standards (AIUM/NEMA, "Acoustic Output Measurement Standards" (1997) http://www.nema.org/stds/ud2.cfm; and AIUM/NEMA, "Standard for Real Time Display of Thermal and Mechanical Acoustic Output Indices on Diagnostic Ultrasound Equipment" (1996) http://www.nema.org/stds/ud3.cfm)

4. A system with very few control parameters, all recognized by the FDA.

5. A self-actuated pressure roller device for displacement of liquefied fat and smoothening of skin.

6. A chemical for enhancing the metabolization process of the emulsified fat.

7. Timer modulated by system settings enabling the system and recording key parameters, updated via communication to a personal computer.

The overall system entails the following reusable and disposable components:

A. Reusables, such as
small handheld ultrasonic transducer(s) with built in on/off switch.
transmitter with MI, TI and focus controls, with temperature, MI, TI and time displays and interface to a personal computer.
personal computer installation software for communication with transmitter.
self-actuated pressure roller device.
B. Consumable/disposable kit, such as
disposable drapes for cover.
surgical coupling gel and rejuvenating cream.
chemical compound for enhancing the natural metabolization of the emulsified fat.
an injection needle.
Core External Ultrasound Lipoplasty Technology To develop a better understanding of our core technology and subsequent design of the product systems, it is important to understand the scope of current ultrasound technology and its design.

Cavitation and localized heat are the most important mechanisms through which ultrasound causes tissue damage. While these effects are avoided in diagnostic ultrasound procedures, they are specifically enhanced, to a certain level, in high intensity focused ultrasound (HIFU) therapeutic, phacoemulsification and ultrasound-assisted lipoplasty (UAL) systems.

Cavitation refers to the oscillatory growth of vapor filled bubbles and their subsequent violent collapse (transient cavitation) resulting in cellular fragmentation of adipocytes and diffusions of lipid material into the intercellular spaces. The other biological effect of ultrasonic energy to consider is the thermal component. All the acoustic energy is eventually transformed into thermal energy, which is concentrated in the focal zone of the acoustic beam. This thermal energy further contributes to the cavitation phenomenon emulsifying more fat at the site and lowers its viscosity, whereas the thermal energy must be kept under control to avoid indiscriminant cell death.

Based upon these principles, the ultrasound-assisted lipoplasty was conceived and designed. Ultrasound-assisted lipoplasty emulsifies adipose tissues with high intensity ultrasound by using 25 to 30 KHz ultrasound transmitted via a titanium cannula. The cannula is inserted through skin at the desired site and emulsification of fat is initiated with high intensity sound waves. A UAL procedure normally includes equipment for infiltration of tumescent fluid both prior to the procedure and during emulsification and aspiration of the liquefied fat. The tumescent fluid is used to enhance emulsification via cavitation and reduces the heating. The emulsification occurs specifically around the cannula tip and the geometry of the removed fat is fan shaped cylindrical tunnels with their origin at the incision.

The current external ultrasound-assisted lipoplasty (known as E-UAL) typically consists of softening adipose tissue by externally applying high intensity ultrasound and removing the softened fat by a standard lipoplasty suction cannula. The current technology uses 1 to 3.5 MHz frequency similar to therapeutic ultrasound with the depth of the sound energy not properly optimized. Thus, the current E-UAL clearly does not demonstrate to be an efficacious procedure for liposuction. Another technology known as high intensity focused ultrasound (HIFU) is currently used for treating prostate cancer using hyperthermia as the ablation method. However, with some modifications this high intensity focused ultrasound technology can be used for lipoplasty procedure.

Dynamically Focused Cylindrical Array Transducer

The primary concept behind our technology and device is the use of a dynamically electronically focused cylindrical array type transducer capable of transmitting ultrasonic waves in the low megahertz frequency range for emulsification of fat cells. The transducer is applied directly above the area where fat is to be melted. Depending upon the volume and depth of the fat layer to be emulsified the transmitter is set by the user for the appropriate amplitude, pulse length, pulse repetition frequency and focus. The sound energy is by design limited to emulsify fat from about 2 mm to about 20 mm in depth. Deeper lying fat can be emulsified at subsequent patient visits once the top layer has been metabolized. The maximum amount of fat being disrupted in one treatment session is approximately 500 cc. The treatment will take approximately 45 minutes and due to the small transducer footprint, almost any area of the body can be targeted.

The emulsified fat cells flow into the body's inter-cellular cavity and within seven to fifteen days they are eliminated from the body through its lymphatic and immune systems.

The design of the device is unique as it considers an optimum frequency, aperture size, focal length, transmission amplitude and pulse length (or pulse repetition frequency). Controlling these properties, through FDA recognized parameters insures optimum speed of the procedure and discrimination of the fat as the destroyed tissue, while maintaining safe levels for other tissues. Furthermore, the design provides a great control in keeping a balance between cavitation and thermal heating by indirect user control of pulse length (or pulse repetition frequency). The emulsification will be achieved without the use of any tumescent fluid. A very large aperture with a short focal length will emulsify fat only in the target area. Specialized transducers for certain parts of the face would be developed for subsequent system generations based on customer feedback.

To facilitate viewing the treatment area before and after lipolysis, a commercially available low cost Diagnostic Ultrasound Imaging System can be used.

In summary, the EUL system of the present invention provides a user friendly, less expensive, safe and effective device for "lunch hour" liposuction.

Ultrasound Transducers and Applications

The diagnostic ultrasound application has created a number of different types of transducers such as: a) single element mechanical wobble, b) annular array mechanical wobble, c) linear array, d) curved array, e) phased array and some subgroups within the linear array family. The most common array type within this subgroup is the 1D (1-dimensional) linear array, which as the active elements has a rectangular PZT element transversely cut into N (typically 128, 144, 192 or 256) elements, which when electronically grouped and phased can create a focused beam and can create a scan when this group of elements is moved by, for example, an element spacing at a time creating a 2D rectangular image (taught by Hoelzler in U.S. Pat. No. 4,164,213, entire contents of which are incorporated herein by reference).

Another array type in this sub group is the 2D (2-dimensional) array, which as the active elements has a rectangular or square PZT element transversely cut two perpendicular directions into N×M (typically 32×32 or 48×48) elements, which when electronically grouped and phased can create a focused beam in any direction with a potential for 3D sector images. In between the 1D and 2D is a so-called 1.5D linear array, which has active elements as the 1D array, but also cut longitudinally and electronically paired so a transverse (out-of-plane) focusing (without beam steering) can be utilized by any combination of phasing and aperture growth including apodization (amplitude weighing of aperture). A manufacturing method of both the 1.5D and 2D array types is taught by Venkataramani in U.S. Pat. No. 5,704,105, entire contents of which are incorporated herein by reference.

In the following sections, a 1.5D transducer without the transversely cut imaging elements will be called a 0.5D transducer and will be referenced as such in the following.

The transducer of the detailed embodiment is illustrated in FIG. 5 through FIG. 8. The transducer has six piezoelectric (active) elements cylindrically placed to focus in the middle of the desired depth. The elements are electrically paired to create three electrical elements for focusing through time delay and/or apodization (amplitude weighing of aperture). The piezoelectric elements are typically made of lead zirconate titanate (PZT).

Figure 5:
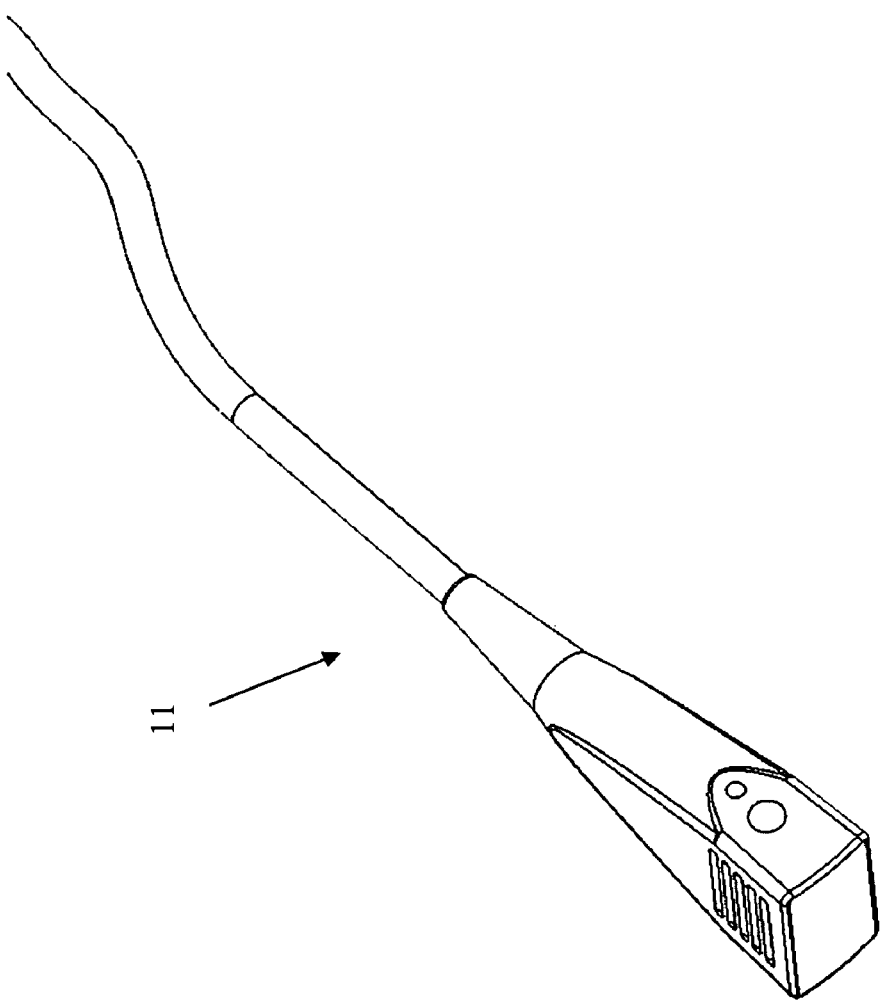
FIG. 5 depicts the external shape of the handheld transducer with the concavity filled in with a material that aid in the focusing of the sound and externally is slightly convex to minimize entrapment of air bubbles during the procedure.
Figure 6:
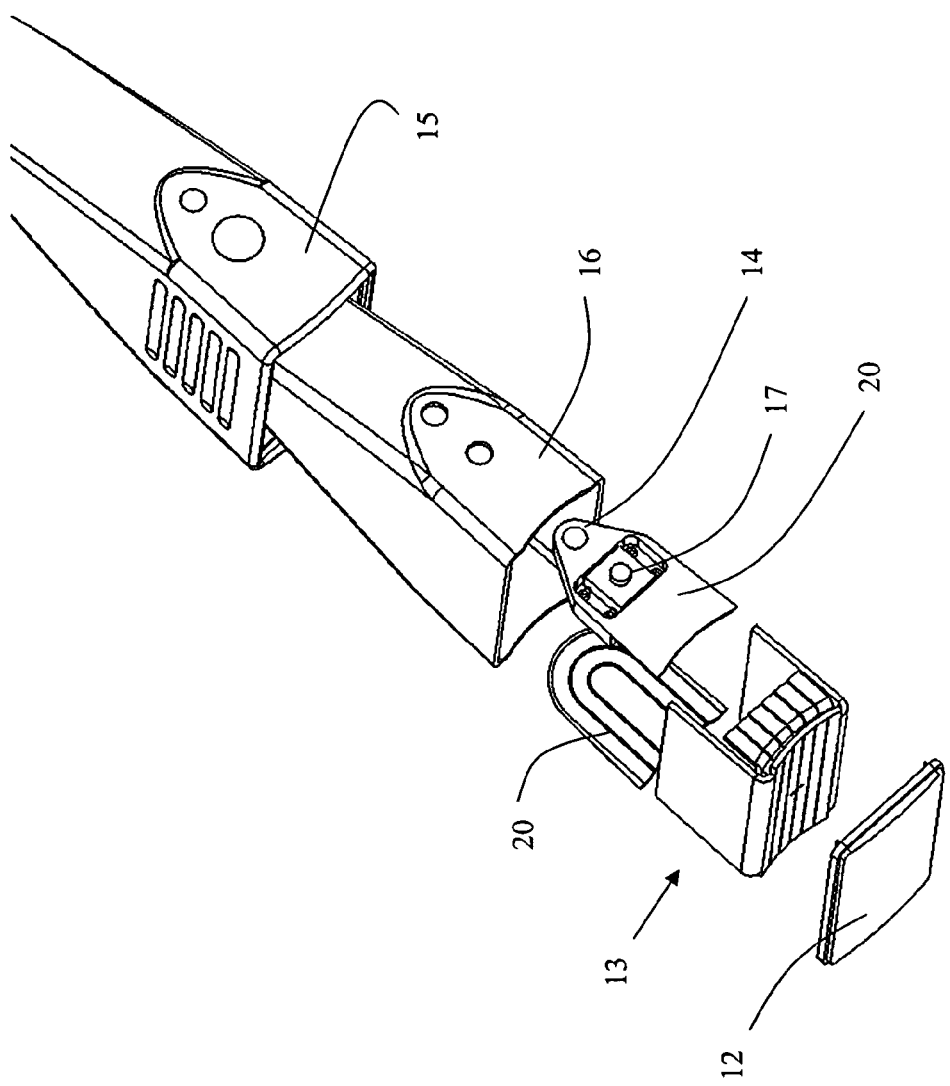
FIG. 6 shows the internals of the transducer, which from left to right are the lens (cavity filler), the front quarter wave matching layer acting as a electrical and thermal conductor, the PZT elements, the back quarter wave matching layers also acting as an electrical and thermal conductors, the small PC-board pairing the elements, the other PC board with on/off switch and LED indicator, the internal shield also acting as a heat sink covering the inside of the housing and the housing.
Figure 7:
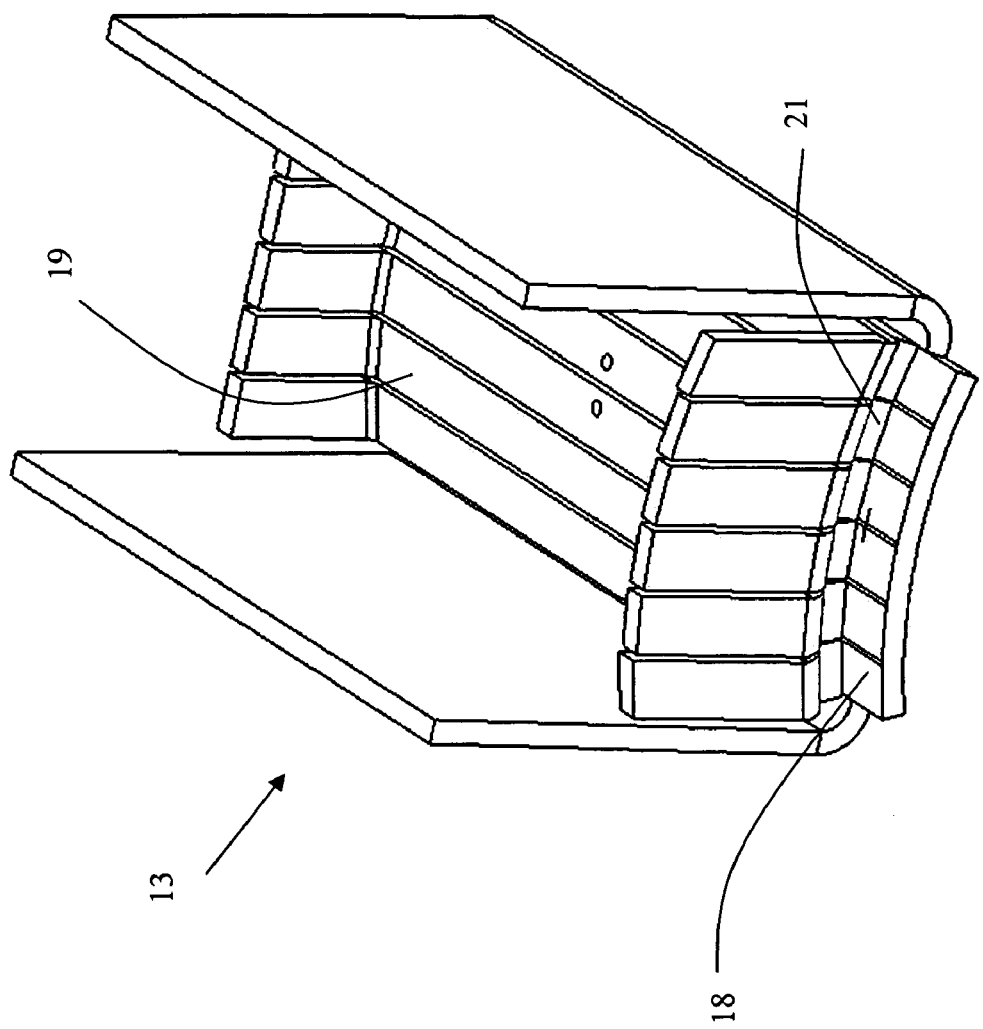
FIG. 7 shows a close-up view of the PZT stack, where the dual conductivity function of the matching layers can easily be envisioned. The two small holes in the center are for the thermocouple leads, monitoring the transducer face temperature.
Figure 8:
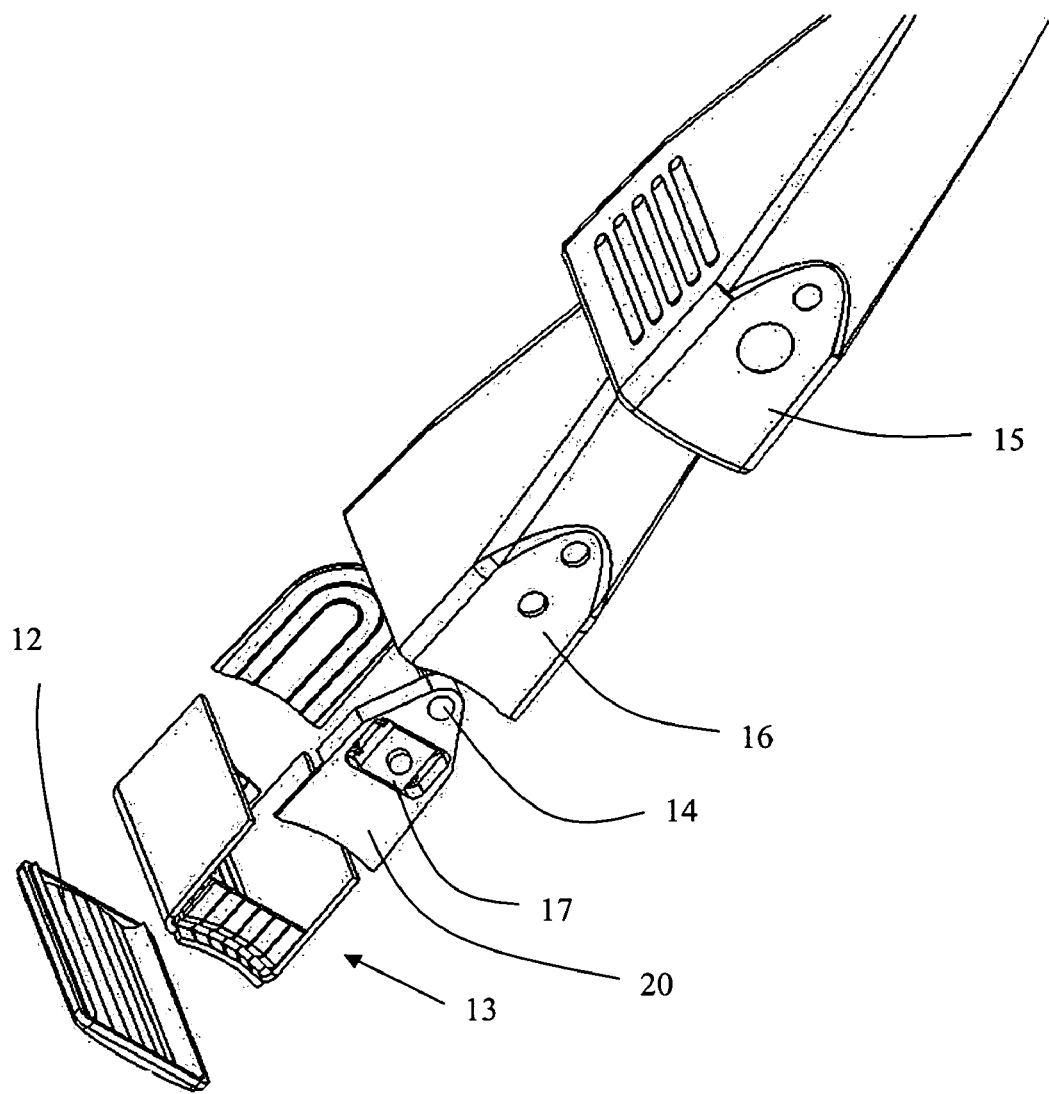
FIG. 8 shows a view from a different angle of FIG. 6.

FIG. 5 shows the assembled transducer (without connector), which has a footprint of 33 mm×20 mm. The transducer 11 shown in "exploded view" in FIG. 6 exposes the lens 12, the PZT stack 13, the switch 17, the LED 14 and the housing 15 with inner shield 16. The PZT stack 13, for example, is shown in FIG. 7 with front 18 and back matching layers 19 serving both as electrical and thermal conductors. The front matching layer is a continuous ground, the back layers are six individual electrically paired strips (with approximate dimensions of 1×2×20 mm) and in between are six PZT elements 21. FIG. 8 shows a close-up of the PZT stack 13 with connector end plates 20, one of which contains the on/off switch 17 and the LED indicator 14.

Figure 9:
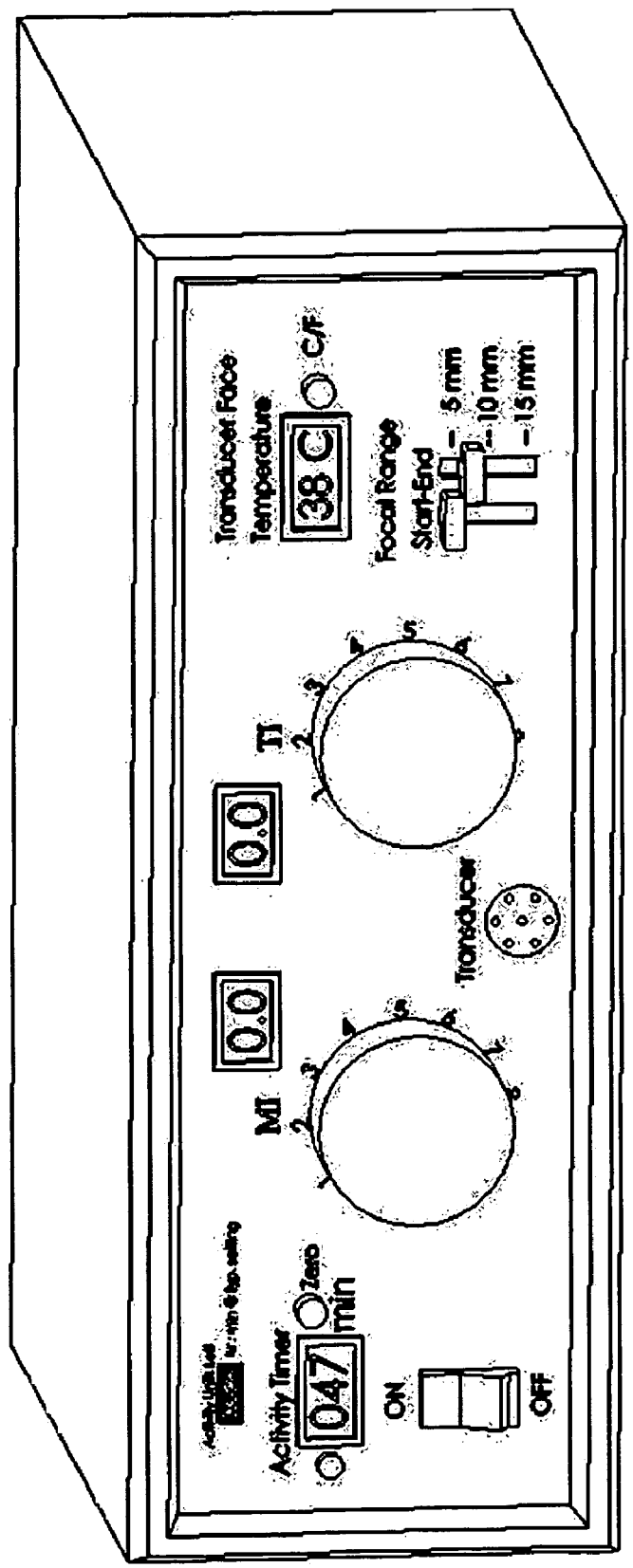
FIG. 9 shows the transmitter (console) with the display and control of the various functions.

The transmitter (console) is depicted in FIG. 9 with a front panel showing control of main power on/off, MI, TI and focus start- and end-depth; the values of MI, TI, the transducer face temperature and time in use are displayed. In addition, the temperature units can be switched between Centigrade and Fahrenheit and the activity timer can be reset.

There are a number of options in designing an optimal ultrasound system for EUL. A single element transducer design is low cost, but has a fixed focus, therefore requiring the user to have a transducer for each focal depth needed. A multi-element transducer with beam steering is convenient to use, but both the transducer and the electronics are costly. The best compromise appears to be a design where the focus is electronically controlled (classified as a 0.5D array). Since the amount of fat reduction is targeted to be less than 500 c.c. per treatment, the focal depth requirements can be limited to be between about 2 and about 20 mm, thus the number of electrical elements (and transmitter channels) can be limited to 3 to 5 (for a 2 MHz system), which still is a cost-efficient solution. A focal "sweep" within the desired focal range, similar to multi-zone focusing for a diagnostic ultrasound system, is a further worthwhile enhancement.

Figure 10A:
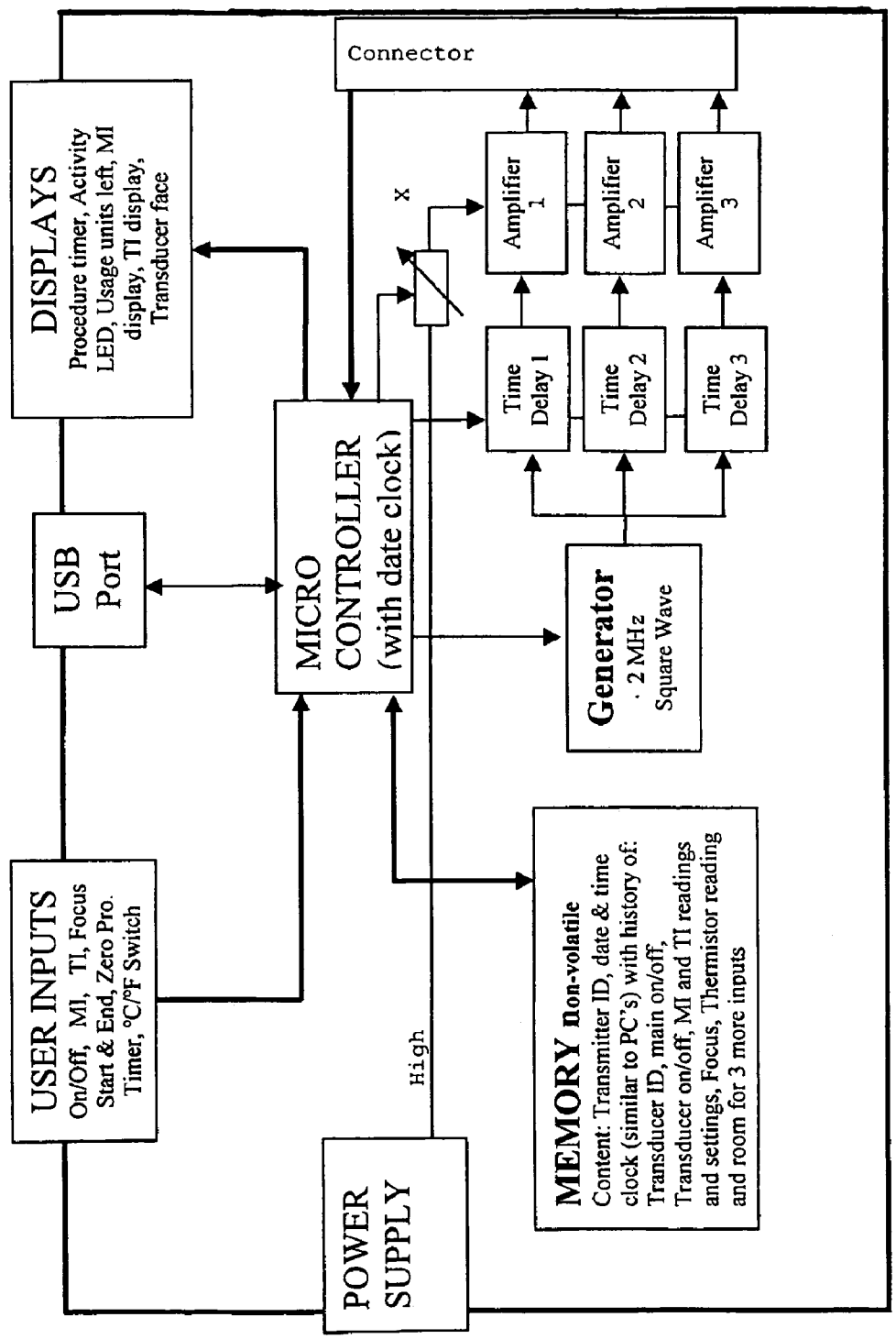
FIGS. 10A and 10B show a system block diagram of the present invention.
Figure 10B:
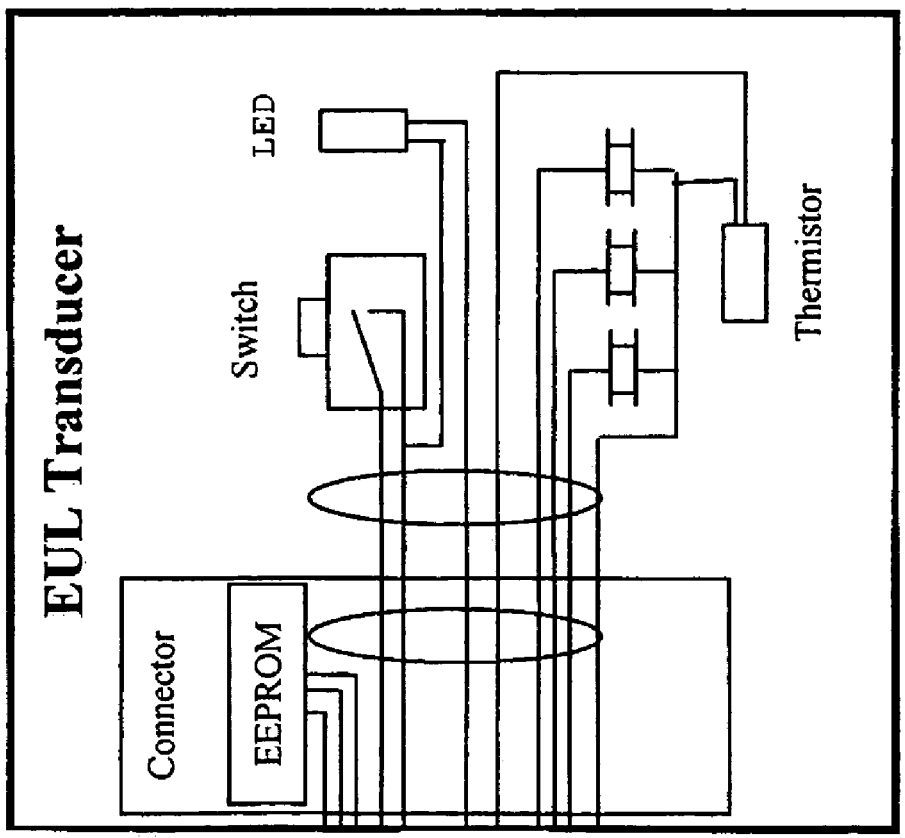

The functional block diagram for the preferred embodiment of the system is shown in FIGS. 10 A and B. Referring to the "User Inputs" functional block, the MI (Mechanical Index) controls transmit voltage, TI (Thermal Index) controls pulse length (PL) and/or Pulse Repetition Frequency (PRF), both at each focus setting are modified by transducer characteristics, which is stored in the EEPROM.

The "USB Port" communicates with the memory through the micro-controller (MC), which in turn would disable the system if the "usage units" were zero. Usage units can be a simple updateable timer with or without system setting modifications. The core transmitter section consists of a 2 MHz square wave generator modulated by the MC to create the necessary PL-PRF combinations. The square wave is split up in 3 and for focusing purposes, time delayed into amplifiers that drive the transducers electrical elements. The three amplifiers have individual amplitude control through the MC to compensate for the inherent acoustic amplitude differences in the transducers and to provide apodization for beam forming.

Instead of time delays, the generator for 3 square waves can be used for running off the same clock, but phased according to focus needs. The amplifiers simply can be high power transistors or MOSFET's.

Matching and safety circuitry are not shown, but they can be transformers, providing some inductive tuning, while the remaining tuning is contained in the individual transducers. Since the transmit voltage is a (slight, maybe 20%) function of focus its rapid switching puts a requirement on the slew rate of the transmit voltage. The block diagram (for clarity) does not show low voltage lines from the "Power Supply".

It is desirable to have a feedback mechanism that tells the user that fat is being emulsified. This can take the form of a cavitation detector integrated into the transmitter. The cavitation detector can be implemented as a pulse-echo difference detector implemented as follows: The system sends out a short pulse, listens for a short period to include the double travel time to the focus, stores this signal as PE1, then listens for a period at a deeper depth and stores this signal as PE2. Knowing that cavitation bubbles will reflect sound back to the transducer and block the sound transmission, the system then compares the two signals PE1 and PE2 for example by taking the ratio of the RMS values ($PE1_{RMS}/PE2_{RMS}$) and show that cavitation occurs if this ratio exceeds a certain value. The cavitation detector can also be based on comparing the PE1 echo to the transmit voltage.

The beam profiles, contour plots, axial plots, etc. from the pre-focused 0.5D transducers are modeled by reducing the problem to a 2-dimensional model with a string of point-sources distributed on the surface of the flat elements, which again are distributed on an arc (pre-focus). The pressure profiles found through superposition according to Huygens principle.

The transducer may further comprise a filler material in the cylindrical cavity of the PZT acting as a focusing lens. The geometric shape of the lens at the skin interface is (convex) cylindrical with a large ROC for the purpose of avoiding entrapment of air on the skin, which blocks the sound. For acoustic modeling purposes the lens material, the skin and the fat are each assumed to be homogenous layers and the skin-fat interface conforming in shape to the lens curvature. Each tissue type is assumed to be adequately acoustically characterized by their sound velocity and attenuation (absorption only). Refraction is also assumed to be present and follow Schnell's law at the interfaces. The transmission and reflection coefficients at the interfaces are close enough to 1 and 0 respectively, that they can be ignored.

The input parameters to the simulation are listed in Table 1 below. Even though the transducer would run in a pulsed mode, a continuous mode (single frequency) analysis is fully adequate, since the transducer design for efficiency reasons is narrow-band, hence each pulse consists of many cycles.

The first step in the analysis follows the ray tracing from the center of the PZT elements to the desired electronic focal point (equal phase) and finds the needed time delays for each of the elements. The ray paths are found by selecting the appropriate ray with the proper refractions at the acoustic interfaces from a dense fan of rays originating at the focal point. The needed delay is those found by calculating the travel time for each ray.

The pressure is then calculated in a 2D matrix (y and z). Since it is a symmetric problem, only half the data is calculated (for example, only positive y values) and then mirrored to the other half plane for the display. The contribution to each receiver point is found through iterative ray tracing from each point transmitter by first assuming a straight line direction, then correcting by the difference in actual and intended direction (intersection with depth for the receive point). This iteration continues until the difference is less than a certain predefined fraction of the wavelength (i.e. less than the spatial quantization). Once the ray path is found, the path length and therefore the phase of the wave can be found when knowing the time delay of the element. The attenuation through that path is also found. That together with the source apodization, if any, determines the amplitude of the point source. For each receive point the amplitude contribution from each transmit point source is summed. After this is done, the time maximum is found by stepping through one full time cycle in steps determined by the time quantization. The process is repeated for each receive point. There may be sources that due to too large a refraction and would be unable to contribute to a receive point, in which case the algorithm will discount this source element's contribution.

The program first calculates and displays the rays from the center of the elements to the focal point. Then the program is activated to calculate the 2D pressure data, which then is displayed as two contour plots, one relative to global maximum and the other relative to axial pressure. The axial pressure is also displayed in a separate graph.

Figure 4:
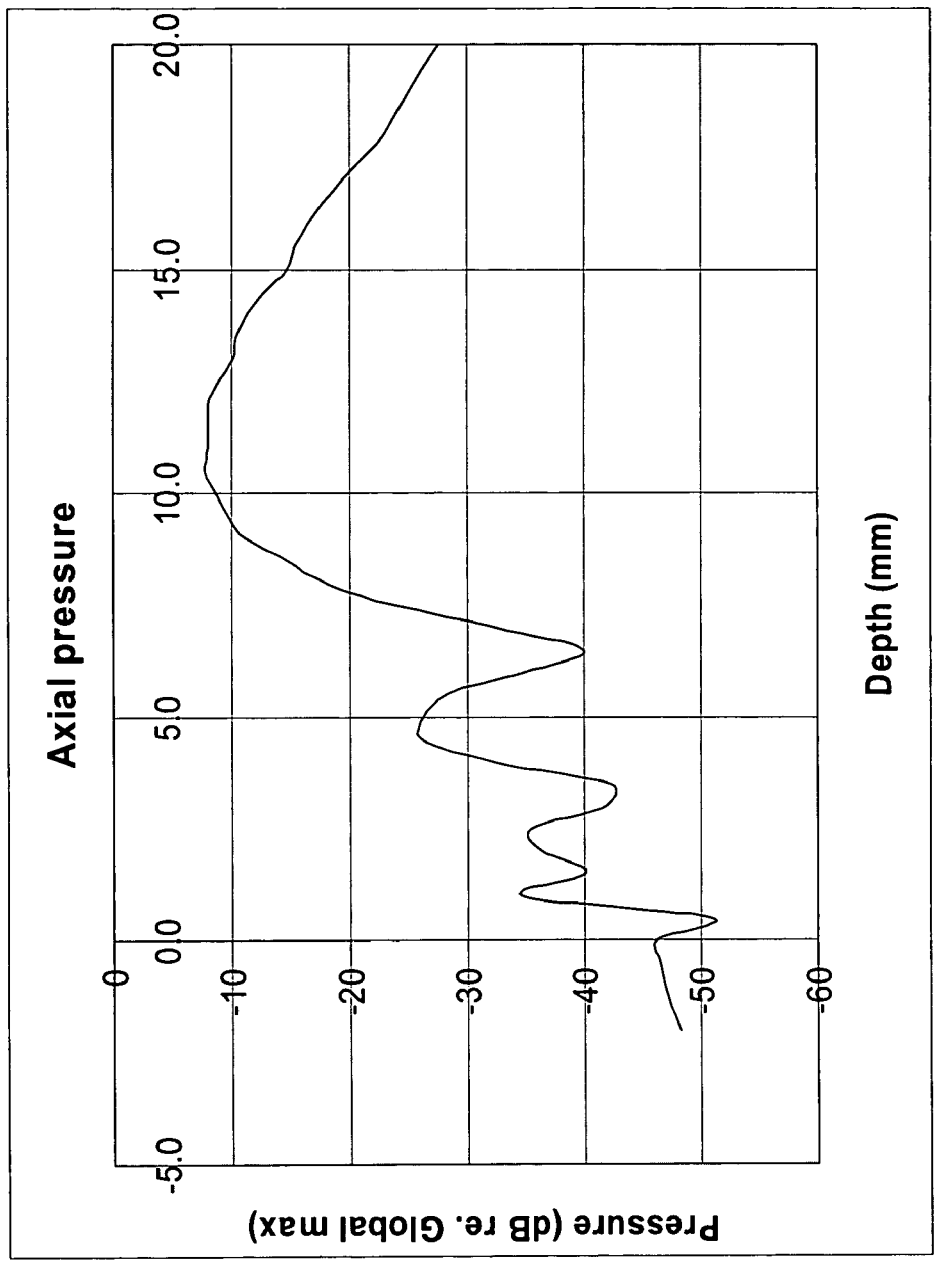
FIG. 4 shows the axial plot of FIG. 2 with the y-axis being the pressure in decibel relative to a global maximum.

The beam forming principle for EUL is the same as utilized in killing tumors with external ionizing radiation, namely by aiming a collimated beam at a single point in space from many angles, thereby reducing the radiation outside the targeted point by $1/r^2$. By using a low F# (defined as focal length/aperture size) the included radiation angle can be up to around 120 degrees (out of 360 degree omnidirectional radiation) reducing the $1/r^2$ dependency. A better description would then be to use the focusing gain, which is the amplitude at the focal point relative to the amplitude at the transducer face and as can be seen in FIG. 4, the focusing gain with the realistic input parameter chosen is about 40 dB, or 100 fold, which is very encouraging for creating cavitation without electrically overdriving the transducer. From that figure the cavitation depth range can also be assessed, for example if the cavitation threshold is 6 dB below the peak amplitude then the cavitation depth range would be approximately 8 mm to 14 mm on the acoustic axis (and less elsewhere).

FIG. 1 shows the paths (sound rays) from the center of the transducer elements to the focal point as they are refracted at the lens-skin and skin-fat interfaces. With some effort, it can be seen that too low a lens sound velocity and/or lens curvature would limit the available aperture.

Figure 2:
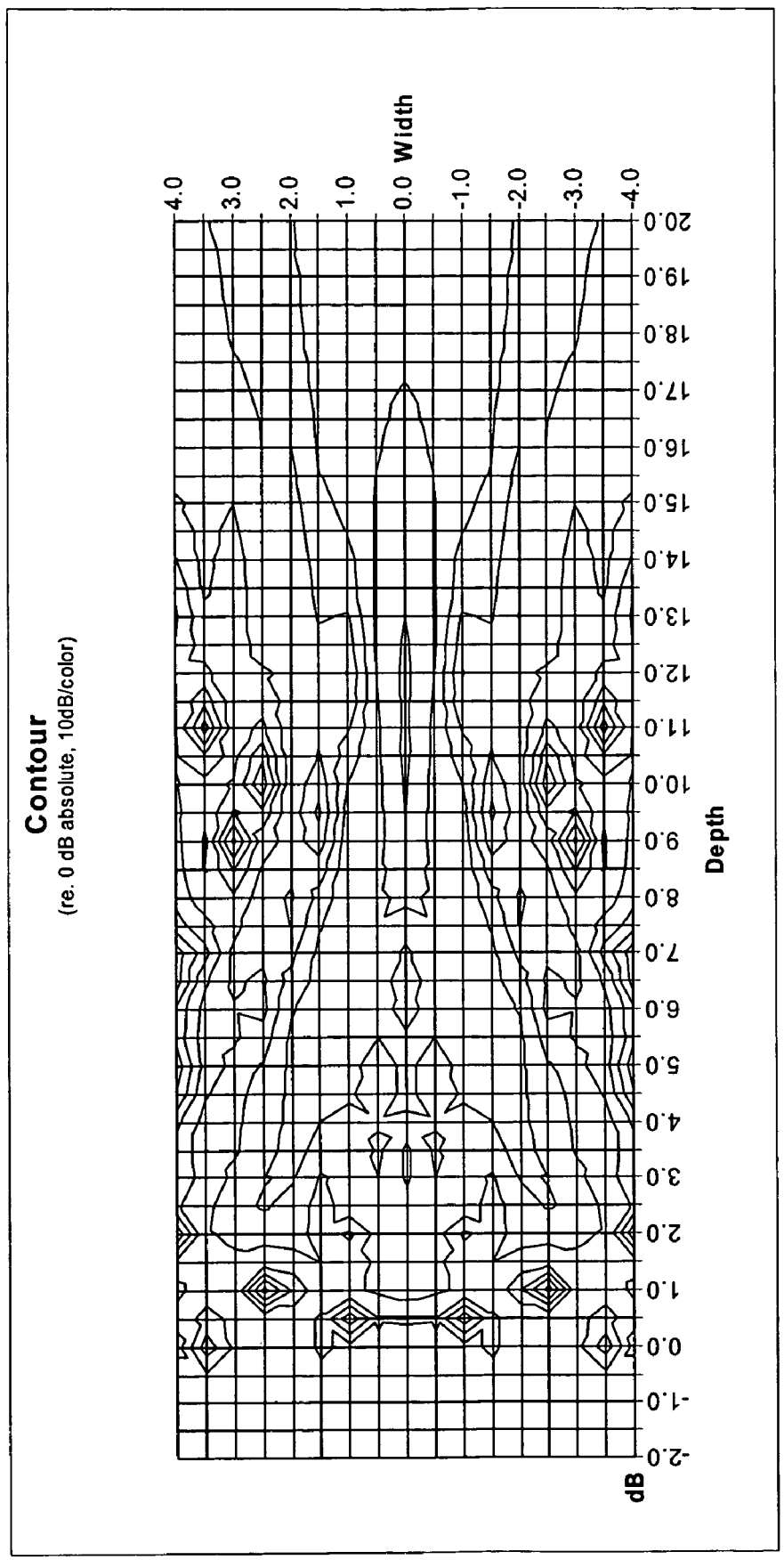
FIG. 2 shows the contour plot of the pressure field relative to a global maximum from a system, transmitter and transducer, with the input parameters listed in Table 1.
Figure 3:
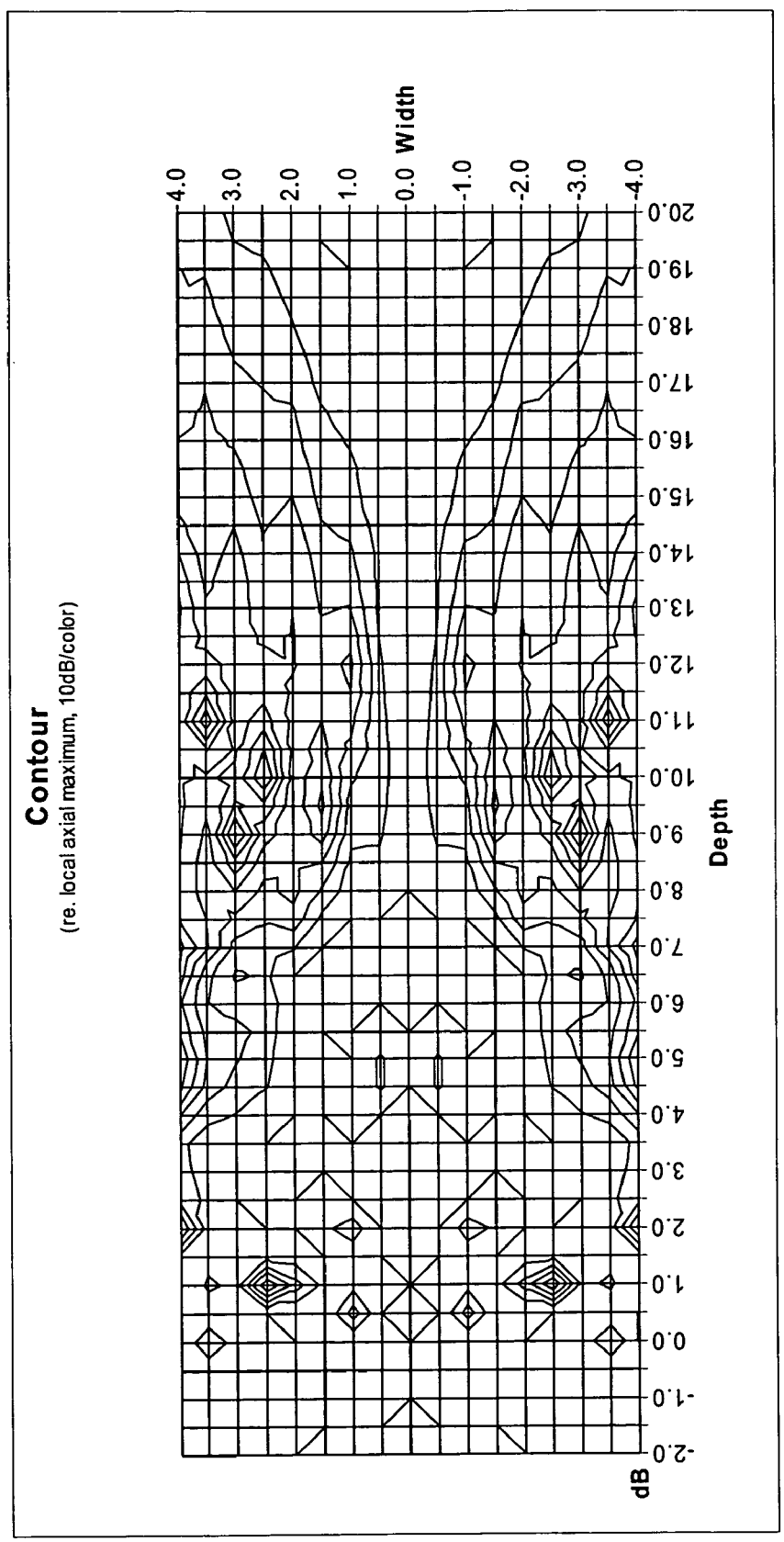
FIG. 3 shows the contour plot of the pressure field as in FIG. 2 except the field is relative to the axial maximum, which better shows beam-widths as a function of depth.

FIG. 2 and FIG. 3 are contour plots of the pressure fields (isobar plots) with FIG. 2 showing the contours relative to the global maximum giving a good impression of the pressure (and intensity) distribution and with FIG. 3 giving a good impression of the beam widths as a function of depth.

The tissue attenuation can be a safety benefit by choosing a frequency in the diagnostic ultrasound range and relying on both beam divergence and attenuation (0.5 dB/cm/MHz) to limit exposure to other organs. Too low a frequency and a large F# will lead to high skin exposure and potential damage. While a small F# and a high frequency is beneficial for a shallow focal range, the direct relationship between cavitation threshold and frequency expressed through the Mechanical Index as $MI=Pr/(f)^{1/2}$, where Pr is peak rarefaction pressure, and f is the frequency, limits the usability of the high end of the frequency spectrum.

In other words the chosen frequency is downwardly limited by the desired size of the transducer (a certain number of wavelengths across the aperture is needed for forming a sharp beam) and upwardly limited by the frequency dependent cavitation threshold.

TABLE 1

Simulation Input Parameters

| Lens | | |
|---|---|---|
| Lens sound velocity | 1 | mm/us |
| Lens attenuation | 2 | dB/cm/MHz |
| Lens curvature, convex | 100 | mm |
| Lens center thickness | 3 | mm |
| Skin | | |
| Skin sound velocity | 1.7 | mm/us |
| Skin attenuation | 0.7 | dB/cm/MHz |
| Skin thickness | 2.5 | mm |
| Fat | | |
| Fat sound velocity | 1.45 | mm/us |
| Fat attenuation | 1 | dB/cm/MHz |
| Transducer | | |
| Aperture size | 12 | mm |
| Frequency | 2 | MHz |
| ROC of element location | 20 | mm |
| Number of electrical elements | 3 | — |
| PZT freq constant ($\lambda/2$) | 2110 | kHz-mm |
| Electronic Focus | | |
| Focal depth (equal phase) | 12 | mm |
| Delay quantization | 30 | ns |
| $1^{st}$ pair delay | 0 | ns |
| $2^{nd}$ pair delay | 30 | ns |
| $3^{rd}$ pair delay | 60 | ns |
| Receive grid | | |
| Receive matrix, width | 8 | mm |
| Receive matrix, depth | 20 | mm |
| Receive matrix, spacing | 0.5 | mm |
| Calculation input | | |
| Time & space quantization | 0.1 | wavelengths* |
| Source quantization | 0.2 | wavelengths* |
| Derived parameters | | |
| Travel time to focus | 11.02 | us |
| Wavelength (in fat) | 0.725 | mm |
| Spatial quantization (in fat) | 0.073 | mm |
| Sampling rate (frequency) | 20 | MHz |
| PZT Thickness | 1.055 | mm |
| ¼ wave aluminum | 0.794 | mm |

*in a 1.5 mm/us medium

Some aspects of the invention relate to a single-channel external ultrasound lipoplasty (EUL) system comprising a transmitter and a single element transducer in the 0.5 MHz to 20 MHz frequency range, consisting of a substantially cylindrically shaped active transducer element with the electronic focus preset by the manufacturer, typically between about 1 mm and 30 mm. The transducer aperture and frequency is chosen, so tissue is not irreversibly affected beyond the manufacturer-selected range when the acoustic pressure and intensity is high enough to emulsify fat within the selected depth range.

Further, some aspects of the invention relate to a multi-channel EUL system comprising a multi-channel transmitter and a multi-channel transducer in the 0.5 MHz to 20 MHz frequency range, consisting of a 0.5D or 1.5D array transducer where the focus is electronically swept within a user or manufacturer selected depth range, typically between about 1 mm and 30 mm. The transducer aperture and frequency is chosen, so tissue is not irreversibly affected beyond the user or manufacturer selected range when the acoustic pressure and intensity is high enough to emulsify fat within the selected depth range.

The multi-channel EUL system has adequate flexibility to emulsify fat MI>1 without significant tissue heating above 39° C. and also functions as a skin tightening device through local heating without emulsifying fat by locally heating tissue above 39° C. with MI<1. It is know that elevated temperature or heating is able to tighten collagen in or around the skin.

In some embodiment, the transmitter of the multi-channel EUL system has independent control of the Mechanical Index (MI) and the Thermal Index (TI) as defined by AIUM/NEMA's Acoustic Output Display Standards. In some embodiment, the transducer has a non-volatile memory (for example EEPROM in the connector) containing necessary electroacoustic information to calculate the MI and TI.

In some embodiment, the transmitter of the multi-channel EUL system displays substantially calibrated values of the MI and TI for each transducer element and setting applied. In one embodiment, the electronic focus (or focusing) is carried out or done by only by electronically delaying (or phasing) the transducer elements. In another embodiment, the electronic focus is carried out or done by only electronically expanding or apodizing the aperture of the transducer elements.

In some embodiment, the multi-channel EUL system is activated by a switch in the transducer or activated by sensing the transducer's contact to the body, for example by sensing impedance change or "ring-down" change.

The transducer's thermal management of the multi-channel EUL system is handled by forced air cooling from the electronic transmitter through the cable (via a hollow tube) into the transducer housing. In one embodiment, the transducer's thermal management is handled through thermal conduction of the inner electrical shield and eventually conducted through the housing surface.

The multi-channel EUL system has a temperature monitoring feature on its face, for example by embedding a thermocouple about the transducer. In one embodiment, the system has real-time display of the transducer face temperature. In another embodiment, the system would be disabled if the transducer face temperature exceeds a predetermined value.

The multi-channel EUL system has a cavitation detection feature based on the pulse-echo signal, as received by the transmitting transducer, from the cavitation bubbles and/or their acoustic shadowing effect at deeper depths.

Some aspects of the invention relate to the transmitter of the multi-channel EUL system having a "system use counter" which monitors the use of the system and will disable it if a certain time and acoustic activity combination (use-time) quota (as predetermined and programmed into the system) has been exceeded. In one embodiment, the multi-channel EUL system has a use-time quota that can be updated. In another embodiment, the "system use counter" is connected to a personal computer (PC) interface, which in turn through communication with a PC can update the use-time quota (instructions download from PC to transmitter). In a further embodiment, the "system use counter" of the multi-channel EUL system can upload system information to a computer (PC). The personal computer interface may include portable memory between a computer and an EUL system (such as a floppy disk, tape, USB memory stick and the like). In one embodiment, an encrypted file is emailed to the user, who then can transfer that file from a PC to his EUL system via a USB memory stick (or a USB cable).

Some aspects of the invention relate to a method for emulsifying subdermal fat of a patient in the 1 mm to 30 mm depth range by topically applying a hand-held high intensity focused ultrasound transducer acoustically coupled to the skin via a liquid or gel. The transducer aperture and frequency is chosen, so tissue is not irreversibly affected beyond the user or manufacturer selected range when the acoustic pressure and intensity is high enough to emulsify fat within the selected depth range. In one embodiment, the method for emulsifying fat, in addition to topically applying ultrasound through a hand-held high intensity focused ultrasound transducer, is supplemented with an activity selected from the group consisting of applying a medical diagnostic ultrasound system that can measure the amount of emulsified and metabolized fat utilizing the measurement package build into the diagnostic ultrasound system, applying a tactile measurement system for verification of emulsified fat such as a skin fold caliper, applying a self actuated pressure roller device for the redistribution of liquefied fat and smoothing of skin, applying a chemical solution such as lecithin and aminophiline and introduction method of the solution to the subdermal fat area for further dissolution of the fat, and applying a reagent strip/kit such as a commercially available laboratory kit for urine measurements, for urine monitoring of metabolized fat from the subdermal fat.

In one embodiment, the acoustic coupling gel is a skin rejuvenation gel or cream such as an oligopeptide complex.

From the foregoing description, it will be appreciated that an external ultrasound lipoplasty medical device and methods for effective liposuction have been disclosed. While the components, techniques and aspects of the invention have been described with a certain degree of particularity, it is manifest that many changes may be made in the specific designs, constructions and methodology herein above described without departing from the spirit and scope of this disclosure.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. An external ultrasound lipoplasty (EUL) system comprising a transmitter and a multichannel transducer comprising an electronic focus and operated in a 0.5 MHz to 20 MHz frequency range, wherein the transmitter is configured to multi-zone focus by electronically sweeping the focus of the transducer such that it generates pulses of acoustic energy at different focal lengths at different times within a user or manufacturer selected depth range between about 1 mm and 30 mm during a use by controlling a plurality of attributes selected from the group consisting of an aperture size, a frequency, a transmit voltage, a delay, an apodization, a pulse repetition frequency and a pulse length for each swept depth to not irreversibly affect tissue of a patient beyond the user or manufacturer selected depth range when an acoustic pressure and intensity of said EUL system is high enough to substantially emulsify fat within said selected depth range of the tissue.

2. The system of claim 1, wherein the transducer is a multi-channel transducer with a 0.5D or 1.5D array.

3. The system of claim 1, wherein the transducer has adequate flexibility to emulsify the fat without significant tissue heating above 39° C.

4. The system of claim 1, wherein the transducer functions as a skin tightening device through local heating of the tissue without emulsifying fat by locally heating the tissue above 39° C.

5. The system of claim 1, wherein the transmitter is a multi-channel transmitter that has independent control of a Mechanical Index (MI) and a Thermal Index (TI).

6. The system of claim 1, wherein the transducer has a non-volatile memory containing necessary electro-acoustic information to calculate a Mechanical Index (MI) and a Thermal Index (TI).

7. The system of claim 1, wherein each channel of the multi-channel transducer has a transducer element, and wherein the electronic focus is carried out by electronically delaying the transducer element or expanding the aperture of the transducer element.

8. The system of claim 1, wherein the transducer has a temperature monitoring feature and real-time display of transducer face temperature on a face of said system, and wherein said system is disabled when the transducer face temperature exceeds a predetermined value.

9. The system of claim 1, wherein the transducer has a cavitation detection feature based on pulse-echo signals received by the transducer, the pulse-echo signals being derived from cavitation bubbles or an acoustic shadowing effect of said bubbles within said selected depth range of the tissue.

10. The system of claim 1, wherein the transmitter has a system use counter configured to monitor use of the system or disable the system if a certain time and acoustic activity combination quota is exceeded, wherein said time and acoustic activity combination quota can be updated.

11. The system of claim 10, wherein the system use counter is connected to a personal computer interface, wherein said time and acoustic activity combination quota can be updated through communication with the personal computer.

12. The system of claim 11, wherein system information is uploaded from the system use counter to the personal computer.

13. A method for emulsifying subdermal fat of a patient comprising:
   selecting a depth range within which to focus acoustic energy between 1 millimeter and 30 millimeters;
   topically applying ultrasound through a hand-held high intensity focused ultrasound transducer acoustically coupled to skin via a liquid or gel, said focused ultrasound transducer comprising a transmitter and a multi-channel transducer operated in a 0.5 MHz to 20 MHz frequency range, wherein the transducer comprises an electronic focus; and
   by multi-zone focusing, electronically sweeping the focus of the topically applied acoustic energy within the selected depth range to generate pulses of acoustic energy at different focal lengths at different times and so as to not irreversibly affect tissue of the patient beyond the user or manufacturer selected depth range when an acoustic pressure and intensity of said focused ultrasound transducer is high enough to substantially emulsify said subdermal fat within said selected depth range of the tissue.

14. The method of claim 13, wherein said method further comprises applying a medical diagnostic ultrasound system for measuring an amount of emulsified and metabolized fat from said subdermal fat.

15. The method of claim 13, wherein said method further comprises applying a tactile measurement system for verification of emulsified fat.

16. The method of claim 13, wherein said method further comprises applying a self actuated pressure roller device for redistribution of liquefied fat from said subdermal fat and smoothing of the skin.

17. The method of claim 13, wherein said method further comprises applying a chemical solution and introduction method of the solution to area of the subdermal fat for further dissolution of said fat.

18. The method of claim 13, wherein said method further comprises applying a reagent strip/kit for urine monitoring metabolized fat from said subdermal fat.

19. The method of claim 13, wherein said gel is a skin rejuvenation gel or cream.

20. The method of claim 13, wherein the transducer comprises transducer elements and the electronic sweeping the focus to generate pulses of acoustic energy at different focal lengths comprises electronically delaying the transducer elements.

21. The method of claim 13, wherein the transducer comprises transducer elements and the electronic sweeping the focus to generate pulses of acoustic energy at different focal lengths comprises electronically apodizing an aperture of the transducer elements.

* * * * *